US012191008B2

(12) United States Patent
Timme et al.

(10) Patent No.: US 12,191,008 B2
(45) Date of Patent: Jan. 7, 2025

(54) SYSTEM AND METHOD FOR DISPLAYING INFANT HEALTH INFORMATION IN CONNECTION WITH A NEONATAL WARMER

(71) Applicant: DRAEGER MEDICAL SYSTEMS, INC., Andover, MA (US)

(72) Inventors: Ulf Timme, Havertown, PA (US); Suresh Chinthakunta, Phoenixville, PA (US)

(73) Assignee: Draeger Medical Systems, Inc., Andover, MA (US)

( * ) Notice: Subject to any disclaimer, the term of this patent is extended or adjusted under 35 U.S.C. 154(b) by 399 days.

(21) Appl. No.: 17/113,864

(22) Filed: Dec. 7, 2020

(65) Prior Publication Data
US 2021/0174917 A1  Jun. 10, 2021

Related U.S. Application Data

(60) Provisional application No. 62/944,104, filed on Dec. 5, 2019.

(51) Int. Cl.
  *A61B 5/145*  (2006.01)
  *A61B 5/00*  (2006.01)
  *G16H 10/60*  (2018.01)
  *G16H 50/30*  (2018.01)

(52) U.S. Cl.
  CPC ......... *G16H 10/60* (2018.01); *A61B 5/14542* (2013.01); *A61B 5/742* (2013.01); *A61B 5/746* (2013.01); *G16H 50/30* (2018.01); *A61B 2503/04* (2013.01)

(58) Field of Classification Search
  CPC .... G16H 10/60; G16H 50/30; A61B 5/14542; A61B 5/742; A61B 5/746; A61B 2503/04; A61B 2503/045
  See application file for complete search history.

(56) References Cited

U.S. PATENT DOCUMENTS

2014/0121478 A1*  5/2014  Coelho ............. A61B 5/14542
                                                  600/301
2016/0113559 A1*  4/2016  Lynch .................... A61B 5/748
                                                  600/301

OTHER PUBLICATIONS

"Dawson et al., Defining the Reference Range for Oxygen Saturation for infants After Birth, May 3, 2010, American Academy of Pediatrics" (Year: 2010).*

* cited by examiner

*Primary Examiner* — Carl H Layno
*Assistant Examiner* — Aya Ziad Bakkar
(74) *Attorney, Agent, or Firm* — Design IP

(57) ABSTRACT

A system and method of displaying neonatal health information are disclosed. In one aspect, the method includes receiving data characterizing a start of an APGAR timer; receiving a time value associated with a current time of the APGAR timer; receiving and displaying on an electronic display a plurality of time windows and a corresponding plurality of target values, each of the plurality of target values representing a predetermined blood oxygen threshold value in connection with a corresponding one of the plurality of time windows; receiving and displaying on an electronic display a measured blood oxygen level value; and highlighting, on the electronic display, a first of the plurality of target values and a corresponding first of the plurality of time windows when the time value associated with the current time of the APGAR timer reaches a first time value.

14 Claims, 17 Drawing Sheets

SYSTEM AND METHOD FOR DISPLAYING INFANT HEALTH INFORMATION IN CONNECTION WITH A NEONATAL WARMER

BACKGROUND

In the field of obstetrics and pediatrics, an "APGAR" score is a simple and repeatable method to assess the health of newborn children (i.e., neonates) immediately after birth. A physician determines the APGAR score by evaluating the neonate on five criteria. The five criteria can be summarized as appearance, pulse, grimace, activity, and respiration. The physician judges each criterion on a scale from zero to two, and then sums the five values. The resulting APGAR score ranges from zero to ten. A physician generally performs the APGAR test at one and five minutes after birth, and may repeat the test later if the score is and remains low. Scores seven and above are normal, scores four to six are low and three and scores below three are critically low.

A low score on the one-minute test may show that the neonate requires medical attention but is not necessarily an indication that there will be long-term problems, particularly if there is an improvement by the stage of the five-minute test. If the APGAR score remains below three, such as when measured at 10, 15, or 30 minutes, there is a risk that the child will suffer longer-term neurological damage. The purpose of the APGAR test is to quickly determine whether a newborn needs immediate medical care. An APGAR timer, in its simplest form, is a stop-watch or egg timer that is begun at the time of birth to remind a physician to measure the neonate's APGAR score at predetermined intervals from birth (e.g., 1, 5, 10, 15, and 30 minutes).

Information critical to knowing whether a neonate needs resuscitation is the neonate's blood oxygen concentration (i.e., the concentration of oxygen in a neonate's blood). When an oximeter measures that a neonate's blood oxygen concentration is low, a decision has to be made as to whether to resuscitate the neonate by providing supplemental oxygen to the neonate's blood. There are devices in the art that can automatically provide supplemental oxygen to a neonate upon a low oximeter reading, but providing too much supplemental oxygen can lead to hyperoxia in the neonate, which can be harmful. Accordingly, it is preferable to allow medical personnel in a labor and delivery environment to evaluate the neonate's APGAR score and use their judgment as to whether any action needs to be taken (such as resuscitation). For purposes of the APGAR score, the expected blood oxygen concentration changes (increases) at predetermined time intervals from birth. In the fast-paced environment of a delivery room, it is challenging for medical personnel to quickly and easily determine whether a measured blood oxygen concentration compares to the expected concentration range for the time interval in which the measurement is taken.

Accordingly, there is a need for a way of displaying measured and expected neonate blood oxygen concentrations during the critical first minutes after birth that efficiently enables medical personnel to monitor measured vs. expected neonate blood oxygen concentrations, be alerted if the a measured blood oxygen concentration falls outside of the expected range for that time period, while enabling medical personnel to exercise judgement when evaluating corrective action.

SUMMARY

This application discloses a user interface that is part of a neonatal monitoring system, including a display that includes information related to the APGAR criteria to provide a visual reminder to medical personnel to perform the test, a timer to prevent the medical professional from waiting too long between the first and subsequent test, a reminder of the criteria of the test for the display to highlight important information. All of which may help to reduce the mental load of the medical professionals. Likewise, in the event that responsibilities need to be transferred to another medical professional (e.g., the first medical professional is called away for some reason), the system will enable a smooth transition to the next medical professional.

In view of the foregoing, a method of displaying neonatal health information is disclosed. The method includes receiving data characterizing a start of an APGAR timer; receiving a time value associated with a current time of the APGAR timer; receiving and displaying on an electronic display a plurality of time windows and a corresponding plurality of target values, each of the plurality of target values representing a predetermined blood oxygen threshold value in connection with a corresponding one of the plurality of time windows; receiving and displaying on an electronic display a measured blood oxygen level value; and highlighting, on the electronic display, a first of the plurality of target values and a corresponding first of the plurality of time windows when the time value associated with the current time of the APGAR timer reaches a first time value.

In addition, a system for displaying infant health information is disclosed. The system includes at least one physiological sensor configured to obtain health information from an infant; an APGAR timer for measuring the time elapsed since a birth event; a memory configured to store health information from the at least one physiological sensor; an electronic display having a user interface for receiving commands from a user; and a processor connected to the at least one physiological sensor, the APGAR timer, the memory, and the electronic display. The processor is configured to receive data characterizing a start of the APGAR timer; receive a time value associated with a current time of the APGAR timer; receive and display on the electronic display a plurality of time windows and a corresponding plurality of target values, each of the plurality of target values representing a predetermined blood oxygen threshold value in connection with a corresponding one of the plurality of time windows; receive and display on the electronic display a measured blood oxygen level value; and highlight, on the electronic display, a first of the plurality of target values and a corresponding first of the plurality of time windows when the time value associated with the current time of the APGAR timer reaches a first time value.

BRIEF DESCRIPTION OF THE DRAWINGS

For a more complete understanding of the present invention, reference is made to the following detailed description of embodiments considered in conjunction with the accompanying drawings, in which.

DETAILED DESCRIPTION

Figure 1:
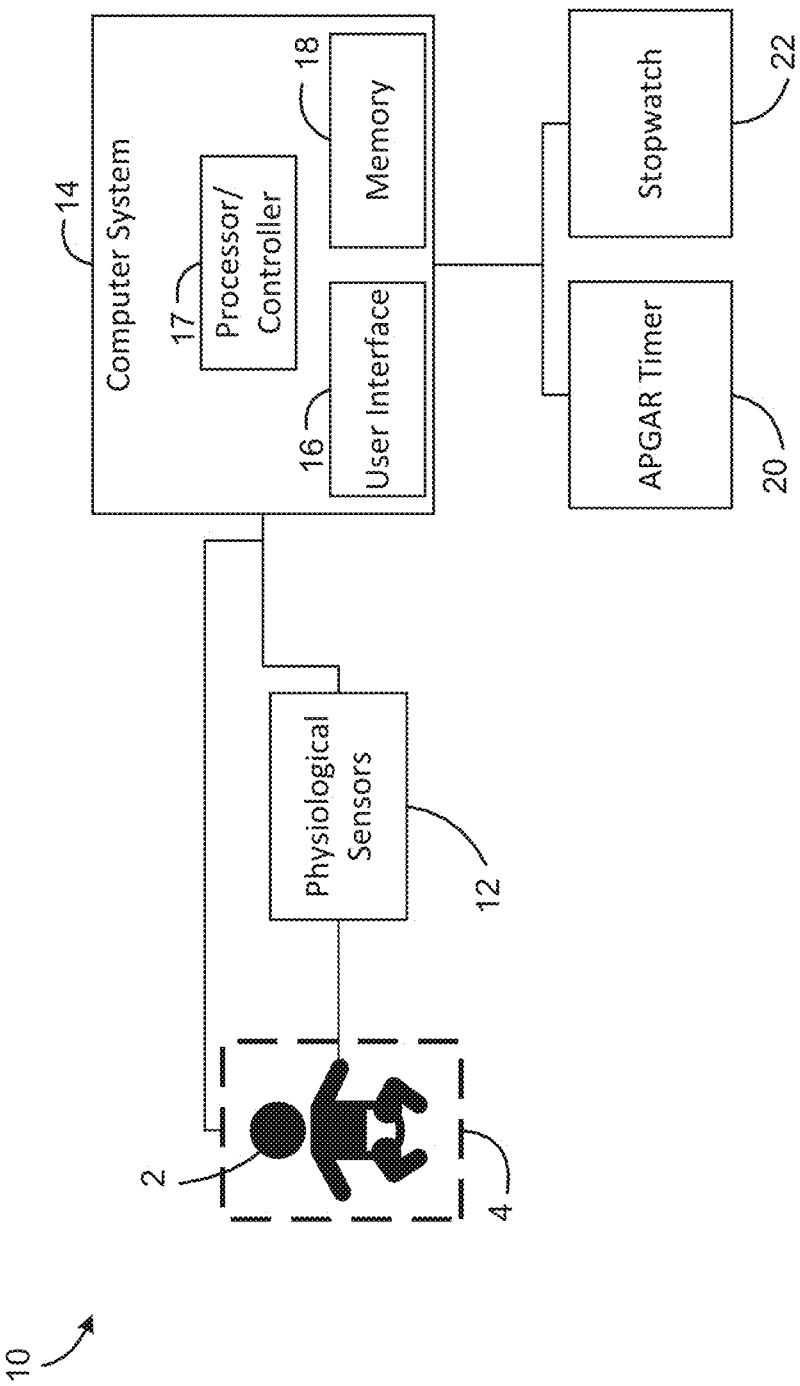
FIG. 1 is a block diagram illustrating a system for displaying neonatal health information in accordance with a first embodiment of the invention.

The following disclosure is presented to provide an illustration of the general principles of the present invention and is not meant to limit, in any way, the inventive concepts contained herein. Moreover, the particular features described in this section can be used in combination with the other described features in each of the multitude of possible permutations and combinations contained herein.

All terms defined herein should be afforded their broadest possible interpretation, including any implied meanings as dictated by a reading of the specification as well as any words that a person having skill in the art and/or a dictionary, treatise, or similar authority would assign particular meaning. Further, it should be noted that, as recited in the specification and in the claims appended hereto, the singular forms "a," "an," and "the" include the plural referents unless otherwise stated. Additionally, the terms "comprises" and "comprising" when used herein specify that certain features are present in that embodiment, but should not be interpreted to preclude the presence or addition of additional features, components, operations, and/or groups thereof.

The following disclosure is intended to be read in connection with the accompanying drawings, which are to be considered part of the entire written description of the invention. The drawing figures are not necessarily to scale and certain features of the invention may be shown exaggerated in scale or in somewhat schematic form in the interest of clarity and conciseness. In this description, relative terms such as "horizontal," "vertical," "up," "down," "top," "bottom," as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise, and includes terms such as "directly" coupled, secured, etc. The term "operatively coupled" is such an attachment, coupling, or connection that allows the pertinent structures to operate as intended by virtue of that relationship.

Referring now to FIG. 1, a system 10 for measuring and displaying neonatal health information in accordance with a first embodiment of the present invention is shown. The system 10 includes a neonatal warmer 4 for receiving a neonatal patient 2 and one or more physiological sensors 12 that measure at least one physiological parameter of the neonatal patient 2. In one embodiment, the physiological sensors 12 includes a pulse oximeter sensor and a temperature sensor. The neonatal warmer 4 and the physiological sensors 12 are coupled, either directly or indirectly, to a computing system 14 which includes a user interface 16 displayed on a display screen, a controller/processor 17 for controlling the display of the user interface 16, receiving information from the neonatal warmer 4 and physiological sensors 12, and receiving and processing commands from the user interface 16, and a memory 18 for storing predetermined values, such as time windows and blood oxygen levels (e.g., SpO2 values), and measurement values received from the neonatal warmer 4 and the physiological sensors 12. SpO2 is a measurement of oxygen being carried in a patient's blood, and is typically presented as a percentage of a maximum amount the blood could carry. Typically, in a healthy adult, a percentage between 96 and 99% is considered normal/healthy. In newborns, however, a lower range (e.g., less than 70%) may be measured initially. It is expected, however, that the SpO2 measurements will increase in the minutes after birth (e.g., a range between 90% and 95% approximately 10 minutes after birth is generally considered normal and healthy). The computing system 14 is connected to an APGAR timer 20 for keeping track of the time elapsed since birth of the neonatal patient 2 and a stopwatch 22 for timing certain events outside of birth chosen by the user, such as a measured SpO2 value at a particular time.

Figure 2:
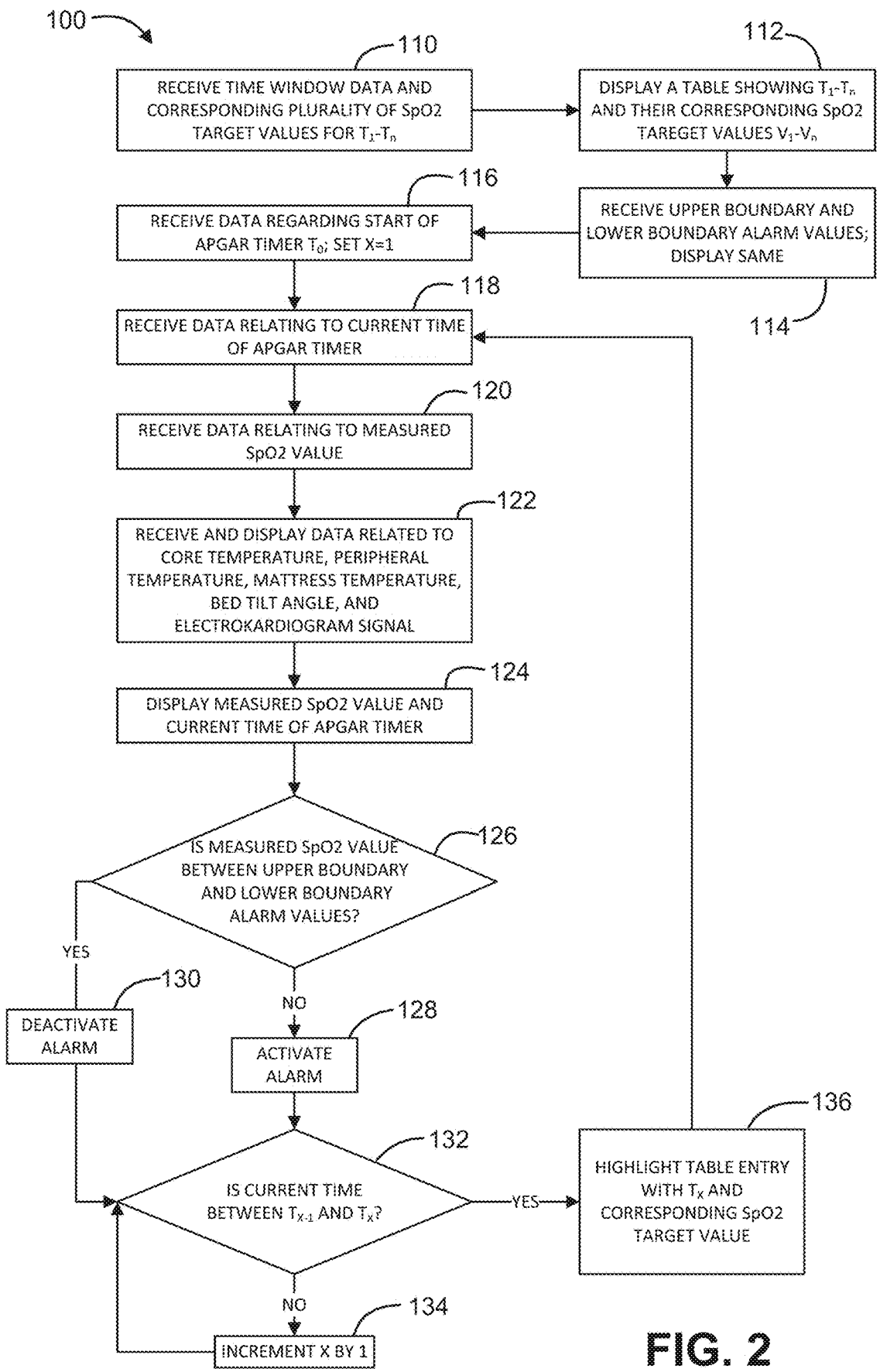
FIG. 2 is a flow chart illustrating a method of displaying a measured blood oxygen value for an infant and target blood oxygen values for the infant at preset times after birth in accordance with a first embodiment of the present invention.

FIG. 2 illustrates a process 100 of displaying neonatal health information using the system 10. At the outset, a user (e.g., a doctor, nurse, medical personnel or technician) may first set up the system 10 by entering into the computing system 14 via the user interface 16 (shown in FIG. 4) a plurality of time windows $T_1$-$T_n$ and a plurality of target SpO2 values $V_1$-$V_n$, each of the plurality of time windows $T_1$-$T_n$ corresponding to time elapsed after the start of the APGAR timer 20, and each of the plurality of target values $V_1$-$V_n$ corresponding to one of the plurality of time windows $T_1$-$T_n$ (step 110; shown in FIG. 4). Once these values have been entered, the system 10 displays a table on the user interface 16 showing each of the time windows $T_1$-$T_n$ and their corresponding target values $V_1$-$V_n$ (step 112). The system 10 also prompts the user to enter alarm values (step 114), namely an upper boundary alarm value and a lower boundary alarm value, that operate to call the attention of the user when a measured SpO2 value of the infant moves out of range of the upper and lower boundary values. These values are also displayed on the user interface 16.

Once the system 10 has been set up, the computing system 14 awaits receipt of a signal or data indicating the start time $T_0$ of the APGAR timer 20 (step 116), which indicates the moment of an infant's birth. In one example, the timer is initiated via a user pressing a button (e.g., a button on the interface 16, a softkey on the system 10, or a hardkey on the system) Thereafter, the computing system 14 regularly receives data from the APGAR timer 20 as to the current time value of the APGAR timer 20 (step 118) along with data from the physiological sensors 12 indicating the current measured SpO2 value of the infant (step 120). In one embodiment, the system 10 also regularly receives data from the at least one physiological sensor 12 regarding other health information about the neonatal patient 2, such as the patient's core temperature, peripheral temperature, and heartbeat, as well as information regarding the neonatal warmer 4, such as the warmer temperature, mattress temperature, and bed tilt angle (step 122), to list a few examples. The computing system 14 then displays this information on the user interface 16 (step 124).

Upon receiving the current time of the APGAR timer 20 at step 118 and a measured SpO2 value of the infant at step 120, the computing system 14 checks for whether the measured SpO2 value is between the upper and lower boundary alarm values (step 126). If the answer is no, the computer system activates an alarm system (step 128) to get the user's attention, which could include commanding the user interface 16 to produce eye-catching graphics, such as flashing colors, or commanding a connected sound system to produce alarm-like sounds, such as a siren or repetitive beeping. If the answer is yes, the computing system 14 moves on and deactivates the alarm system if it is currently activated (step 130). The alarm system, when activated by step 128, is designed to alert the attention of the user when the measured blood-oxygen level of the neonatal patient 2 is at an unsafe level, thereby providing the impetus for the user or other medical personnel to treat the unsafe condition.

After the measured SpO2 value is checked in step 126, the computing system 14 checks for whether the current time of the APGAR timer 20 is within a particular time window, namely between $T_{x-1}$ and $T_x$ (step 132). The computing system 14 first checks whether the current time is within the first time window (i.e., between $T_0$ and $T_1$, where x=1). If the answer is no, the computing system 14 then moves to the next time window (i.e., increases x by 1; see step 134) and then checks whether the current time is within the second time window (i.e., between $T_1$ and $T_2$) (repeat step 132). This continues until step 132 results in a "yes," at which point the table entry with the corresponding $T_x$ and $V_x$ values is highlighted (step 136), thereby calling the attention of the doctor, nurse, or technician to view the target SpO2 value $V_x$ and compare it against the measured SpO2 value of the infant. Steps 118-136 repeat as the APGAR timer 20 continues to run. The term "highlighted", as used in the specification and claims, is intended to mean to make an element of a graphical user interface stand out from other elements of the interface, for example, by showing text or data in a heavier font (bold), providing a different background color than other elements, making a portion of that element flash or sequentially change color or brightness.

Figure 3:
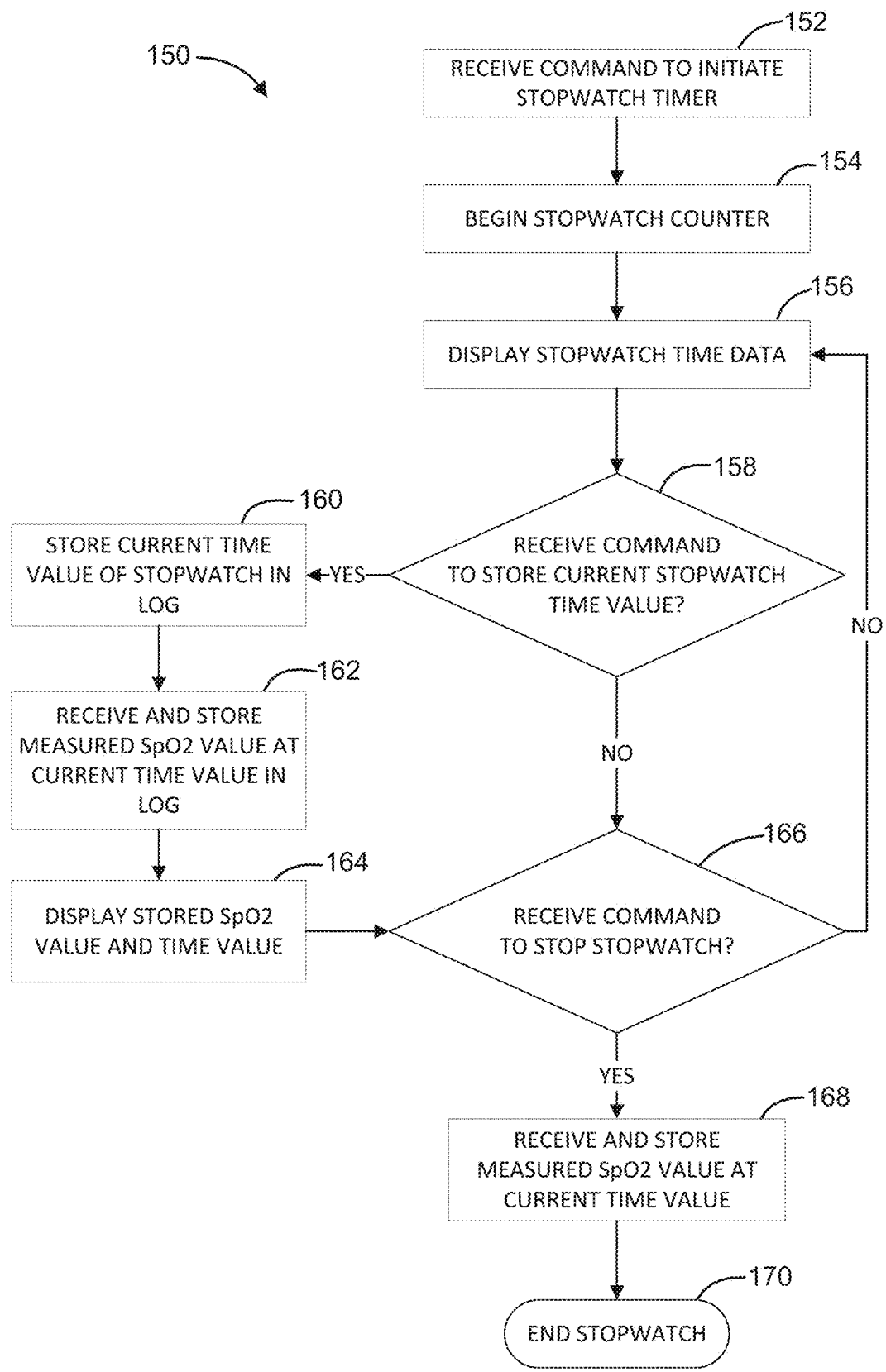
FIG. 3 is a flow chart illustrating a method of logging measured blood oxygen values that correspond to a time value associated with a stopwatch in accordance with a first embodiment of the present invention.

FIG. 3 illustrates a process 150 of measuring and recording neonatal health information based on the readings of the stopwatch 22. At the outset, the computing system 14 receives a command from the user interface 16 to initiate the stopwatch 22 (step 152). The stopwatch 22 can be initiated at any time at the user's discretion, including before the APGAR timer 20 starts or while the APGAR timer 20 is running. Once initiated, the stopwatch 22 begins to count seconds (step 154), and the user interface 16 displays the time elapsed in seconds since the stopwatch 22 was initiated (step 156).

The computing system 14 regularly checks whether it has received a "store" command from the user via the user interface 16 (step 158). When the computing system 14 receives a "store" command, the computing system 14 checks and records the current time value of the stopwatch 22 into the memory 18 (step 160). At the same time, the computing system 14 receives from the physiological sensors 12 a measured SpO2 value representing the blood oxygen level of the neonatal patient 2 at the time it received the "store" command, and then stores the measured SpO2 value with the current time value in the memory 18 (step 162). In one embodiment, the computing system 14 will then display the recorded time values and corresponding measured SpO2 values obtained from each received "store" command (step 164).

Steps 156-164 repeat until the computing system 14 receives a "stop" command from the user via the user interface 16 (step 166), at which point the computing system 14 receives and stores the measured SpO2 value measured at the time the "stop" command was received (step 168). The stopwatch 22 ceases counting and displays the time value the stopwatch 22 had reached upon receiving the "stop" command (step 170).

Figure 4:
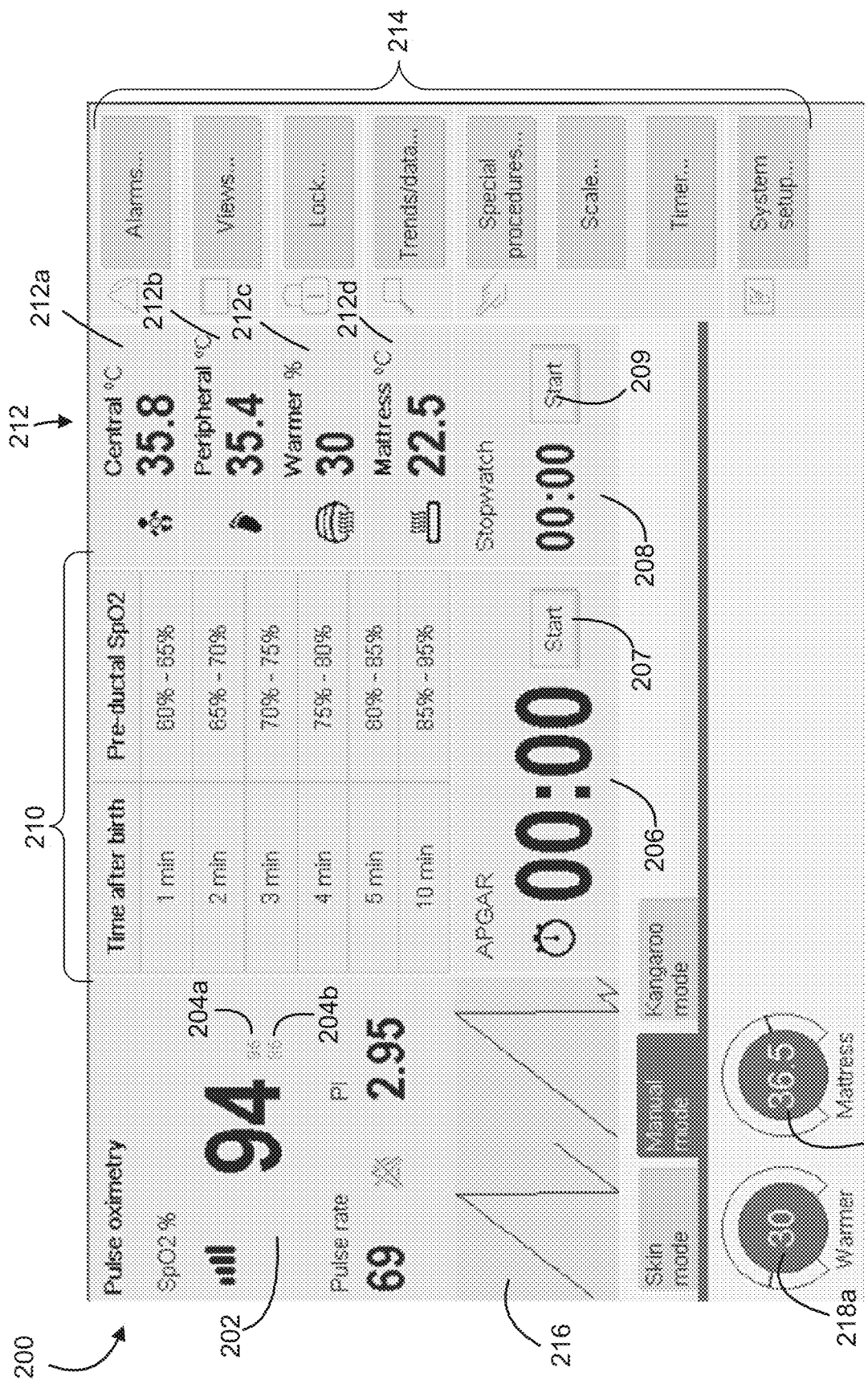
FIG. 4 is a schematic view of an electronic display showing a measured blood oxygen value for an infant and target blood oxygen values for the infant at preset times after birth in accordance with a first embodiment of the present invention, the electronic display showing an APGAR timer at a time of 00:00 and a stopwatch at a time of 00:00.

FIG. 4 displays an exemplary embodiment of a display 200 of the user interface 16 discussed above. As seen in FIG. 4, the display 200 includes a SpO2 monitor 202 that displays the infant's current measured SpO2 value and regularly updates based on the measured SpO2 values it receives from the physiological sensors 12. The SpO2 monitor 202 also displays the upper and lower alarm values 204a, 204b next to the received measured SpO2 value being displayed. The display 200 also includes an APGAR timer interface 206 and a stopwatch interface 208, both of which allowing a user to start the APGAR timer 20 and stopwatch 22, respectively, with the touch of a button (see APGAR timer and stopwatch "Start" keys 207, 209) and monitor the progress of each. Above the APGAR timer interface 206 is a target table 210 showing each of the time windows $T_1$-$T_n$ and their corresponding target values $V_1$-$V_n$, where each time window $T_x$ is positioned on the left side of its corresponding target value $V_x$. To the right of the target table 210 is a sensor monitor 212 showing the one or more other values being monitored by the physiological sensors 12, such as a central temperature monitor 212a which measures the core temperature of neonatal patient 2, a peripheral temperature monitor 212b which measures the temperature of the neonatal patient's extremities, a warmer power monitor 212c which measures the power output of the neonatal warmer 4, and a mattress temperature monitor 212d which measures the mattress temperature of the neonatal warmer 4. The display 200 also includes a configuration button array 214 that a user can touch to configure the system 10 from the user interface 16. In one embodiment, the display 200 also includes an electrocardiogram monitor 216 that shows the heartbeat of the neonatal patient 2 and control dials 218a, 218b for controlling the power output of the warmer and mattress heater.

Figure 5:
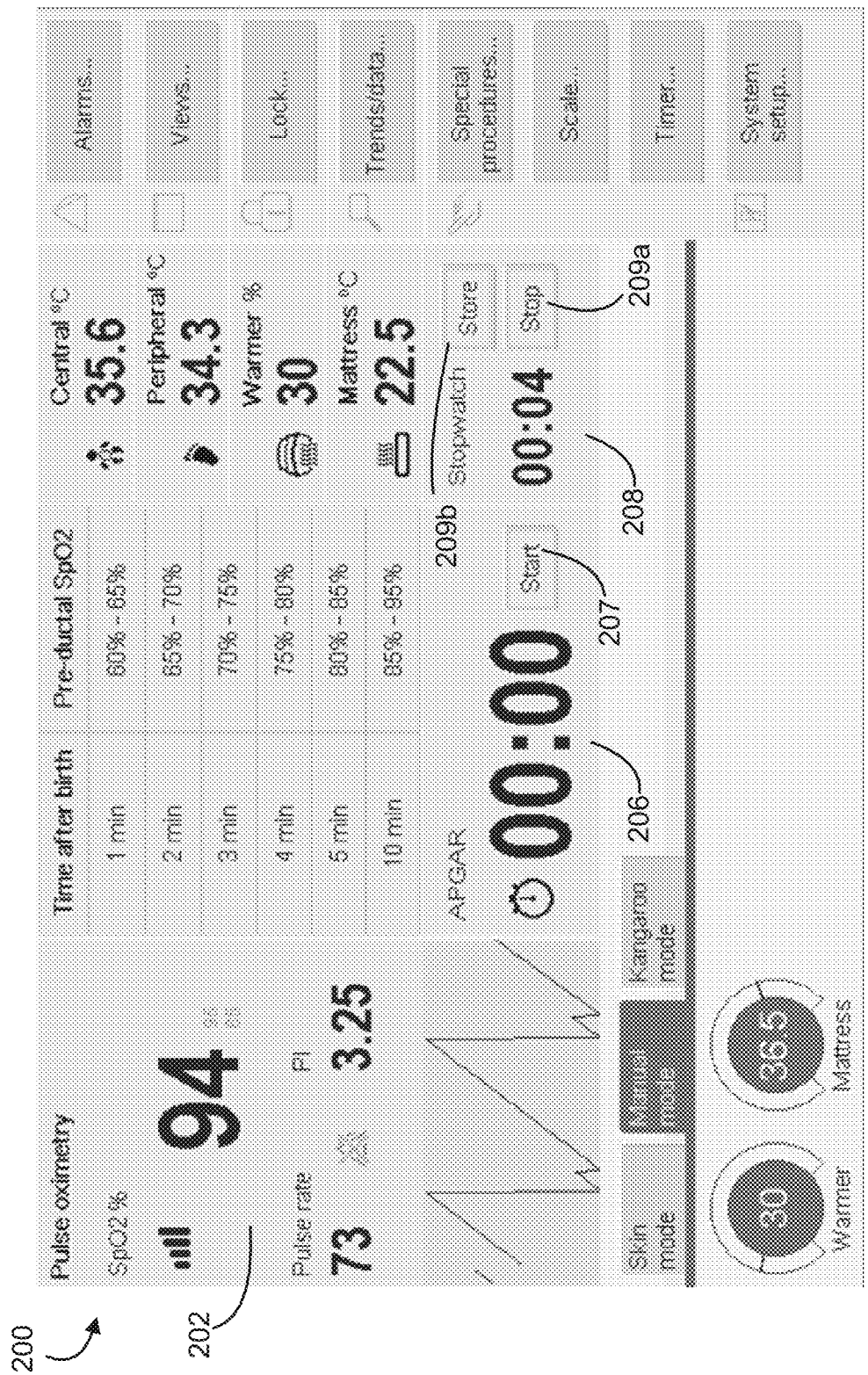
FIG. 5 is the view of FIG. 4 with the stopwatch at a time of 00:04.

Turning to FIG. 5, when a user touches the stopwatch "Start" key 209 of the stopwatch interface 208 (see step 152 of FIG. 3), the stopwatch interface 208 displays an upward counting timer (see step 154 of FIG. 3), the stopwatch "Start" key 209 transforms into a stopwatch "Stop" key 209a, and a stopwatch "Store" key 209b appears. The stopwatch "Store" key 209b sends a command to the computing system 14 to initiate the SpO2 value storing functions of steps 160-164 shown in FIG. 3 and discussed above. When the stopwatch "Stop" key 209a is pressed, the computing system 14 receives a command to stop the stopwatch 22 (see step 166 of FIG. 3).

Figure 6:
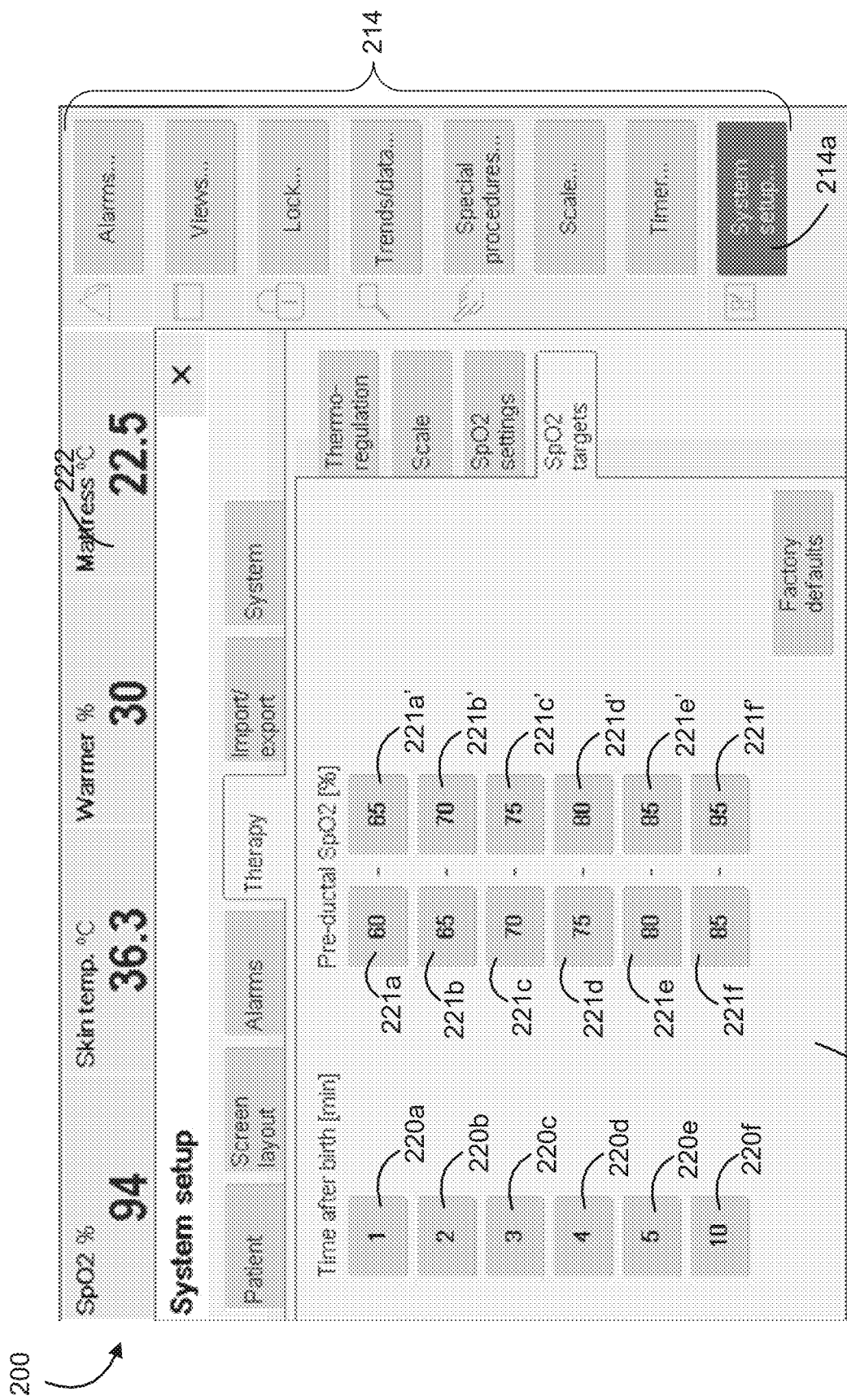
FIG. 6 is a schematic view of an electronic display prompting a user to input preset times after birth and corresponding blood oxygen target values.

FIG. 6 illustrates the execution of step 110 on the display 200. When a user presses the "System setup" key 214a on the configuration button array 214, a system setup window 220 appears to allow a user to configure the time windows $T_1$-$T_n$ and the target values $V_1$-$V_n$ that will be shown in the target table 210. More particularly, the system setup window 220 includes interactive keys that show the currently set time windows (see time keys 220a-220f) and the current target values (see lower target keys 221a-221f and upper target keys 221a'-221f') that will appear in the target table 210. Pressing these interactive keys will enable the user to change the values shown on the face of these keys, which will show on the target table 210 of the display 200 as time windows $T_1$-$T_n$ and target values $V_1$-$V_n$ (see step 112 in FIG. 2).

Figure 7:
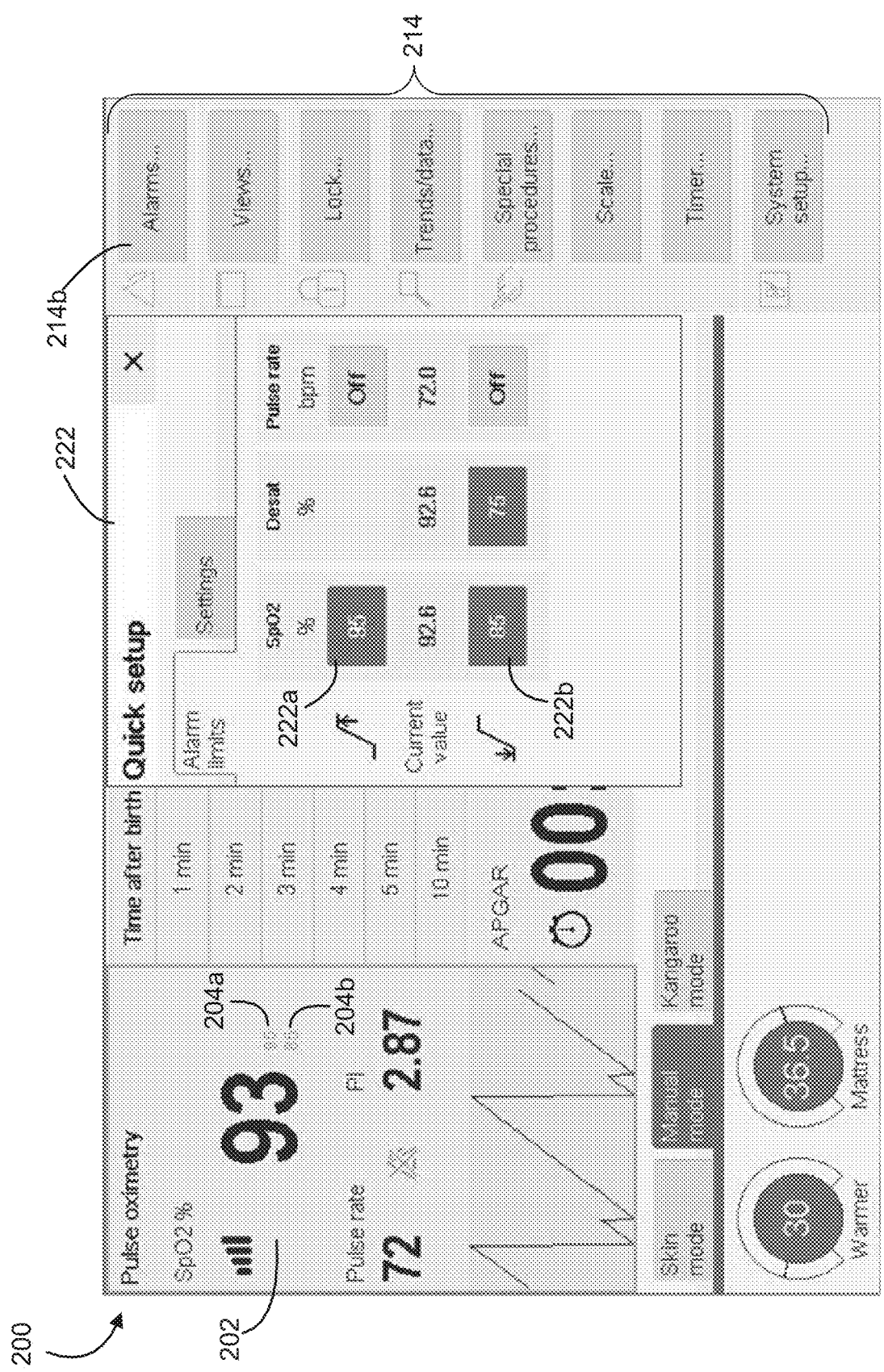
FIG. 7 is a schematic view of the electronic display shown in FIG. 4 showing a window that prompts the user to enter alarm limits.

FIG. 7 illustrates the execution of step 114 on the display 200. When a user presses the "Alarms" key 214b on the configuration button array 214, an alarm setup window 222 appears to allow a user to configure the alarm limits of the system 10. More particularly, the alarm setup window 222 includes interactive keys that show the current upper and lower limit alarm values (see upper limit key 222a and lower limit key 222b) on either side of the current measured SpO2 value (see SpO2 monitor 202). When pressed, the upper and lower limit keys 222a, 222b enable the user to enter a desired upper SpO2 boundary value and a lower SpO2 boundary value, respectively. These values will show on the SpO2 monitor 202 as the upper and lower alarm values 204a, 204b.

Figure 8:
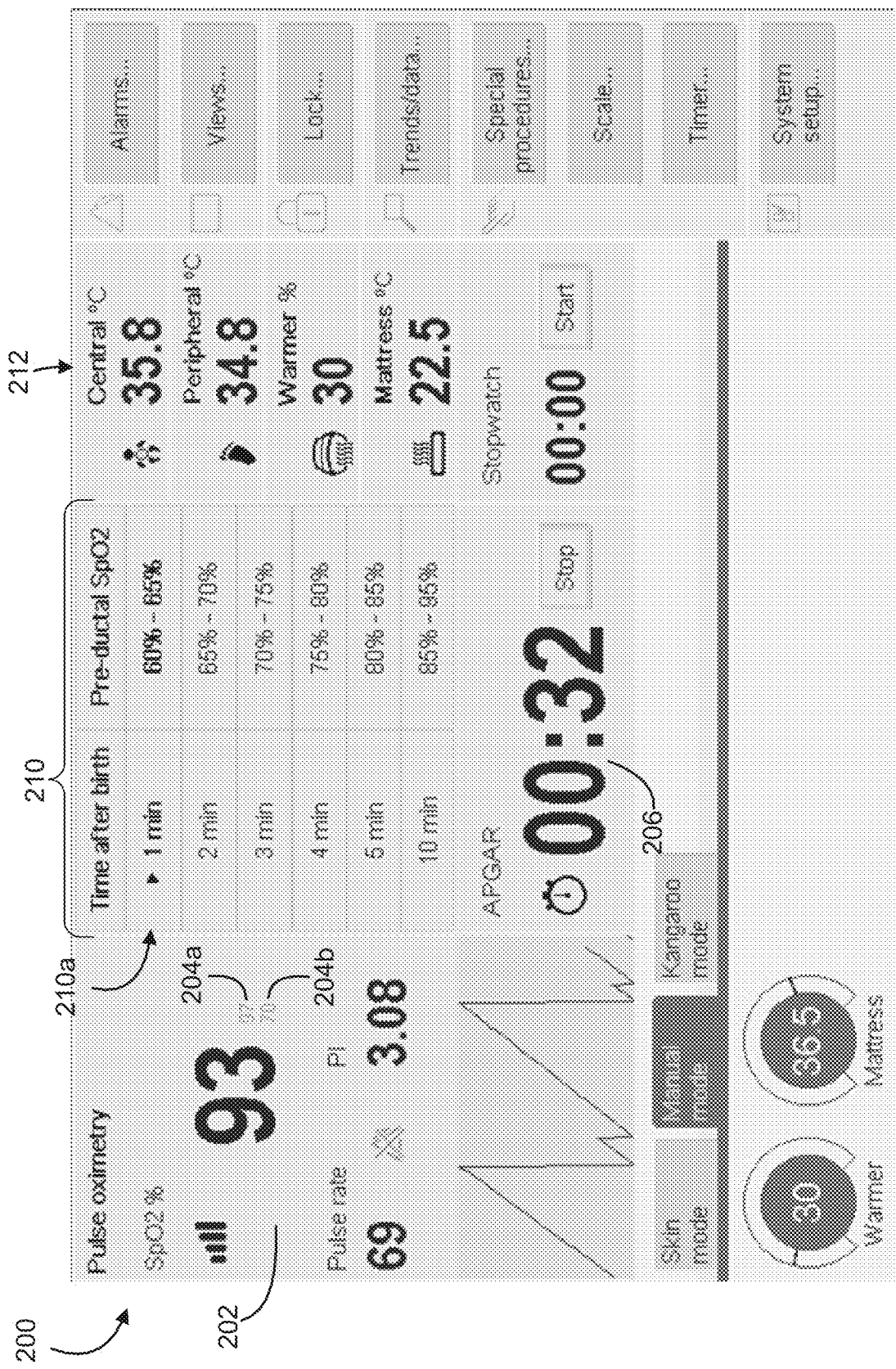
FIG. 8 is the view of FIG. 4 with the APGAR timer at a time of 00:32.
Figure 9:
FIG. 9 is the view of FIG. 4 with the APGAR timer at a time of 02:01, the stopwatch at a time of 07:05, and an alarm being activated.
Figure 10:
FIG. 10 is the view of FIG. 4 with the APGAR timer at a time of 05:11 and a negative condition warning sign being displayed.

FIGS. 8-10 illustrate the execution of step 136 on the display 200. As seen on the APGAR timer interface 206 in FIG. 8, the APGAR timer 20 has already begun and is at 32 seconds. At this point, the computing system 14 has recognized that the APGAR timer 20 is currently within the first time window $T_1$, and has highlighted the first entry 210a on the target table 210 by placing the text thereon in bold. As seen in FIG. 8, the SpO2 monitor 202 indicates that the measured SpO2 value is outside the target values of the first time window, but within the upper and lower alarm values 204a, 204b.

Turning to FIG. 9, the APGAR timer interface 206 shows that the APGAR timer 20 is at 2:01, which the computing system 14 recognizes as no longer within the first time window $T_1$ and now within the second time window $T_2$. Accordingly, the first entry 210a is no longer highlighted, and instead the second entry 210b on the target table 210 is highlighted. In addition, the SpO2 monitor 202 indicates that the measured SpO2 value is not only within the target values of the second time window, but it also exceeds the upper alarm value 204a, which results in an alarm being activated. This alarm can take various forms, including the appearance of an alarm window 224 indicating the cause for alarm or the flashing of the SpO2 monitor, as seen in FIG. 9.

Turning to FIG. 10, the APGAR timer interface 206 indicates that the APGAR timer 20 is at 5:11, which is within the fifth time window $T_5$ as seen on the fifth entry 210e, and the SpO2 monitor indicates that the measured SpO2 value is within the fifth target value. Accordingly, the fifth entry 210e of the target table 210 is highlighted. In addition, a condition warning sign 223 has appeared as a result of one of the control dials 218a, 218b being turned down to an unacceptable level (i.e., below 36 degrees C.). This informs the user of a potential problem, thereby providing the impetus to fix it.

In one or more alternative embodiments, methods for highlighting the time windows could be implemented. For example, previous or subsequent time windows could be "gray out", the current time window may be highlighted via a colored box, subsequent time windows may only "appear" as the timer starts the next time window, to list a few examples. Additionally, one or more of these exemplary embodiments could be combined.

Figure 11:
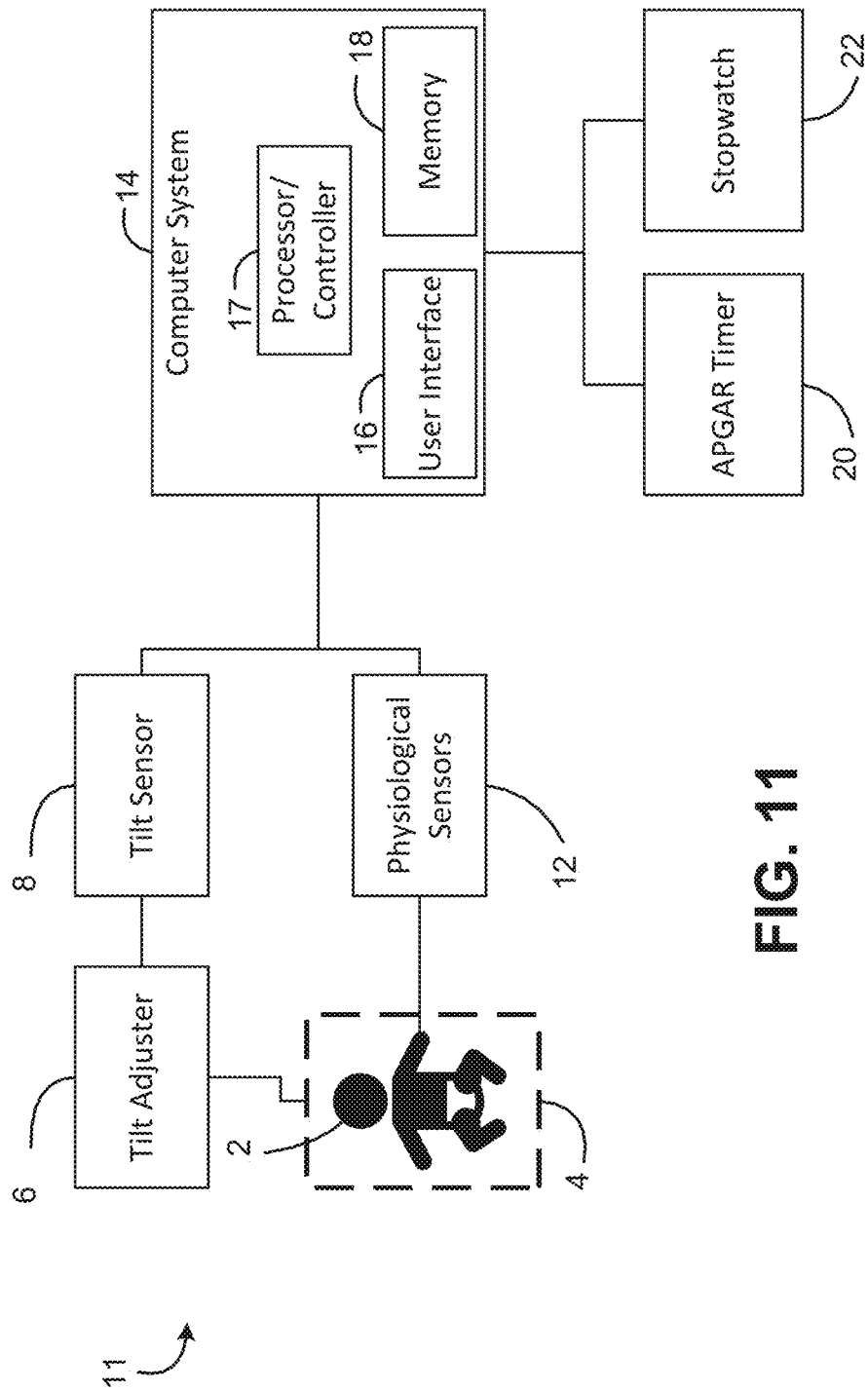
FIG. 11 is a block diagram illustrating a system for displaying neonatal health information in accordance with a second embodiment of the invention.

FIG. 11 shows a system 11 for measuring and displaying health information in accordance with a second embodiment of the present invention. In this embodiment, the neonatal warmer 4 includes a bed tilt adjuster 6 that adjusts the angle at which the bed of the neonatal warmer 4 is positioned relative to a horizontal plane. While not illustrated in the figure, the tilt adjust is able to adjust the neonatal warmer in both the longitudinal and latitudinal axis. The neonatal warmer 4 and the bed tilt adjuster 6 are connected to a tilt sensor 8 which measures the bed tilt of the neonatal warmer 4 and communicates that information to the computing system 14. The controller/processor 17 of the computer system is also configured to send control signals to the bed tilt adjuster 6 to change the bed tilt of the neonatal warmer 4. In one embodiment, the tilt sensor 8 includes one or more accelerometers. The accelerometer could be a multi-axis accelerometer (e.g., 2 axis or 3 axis).

Figure 12:
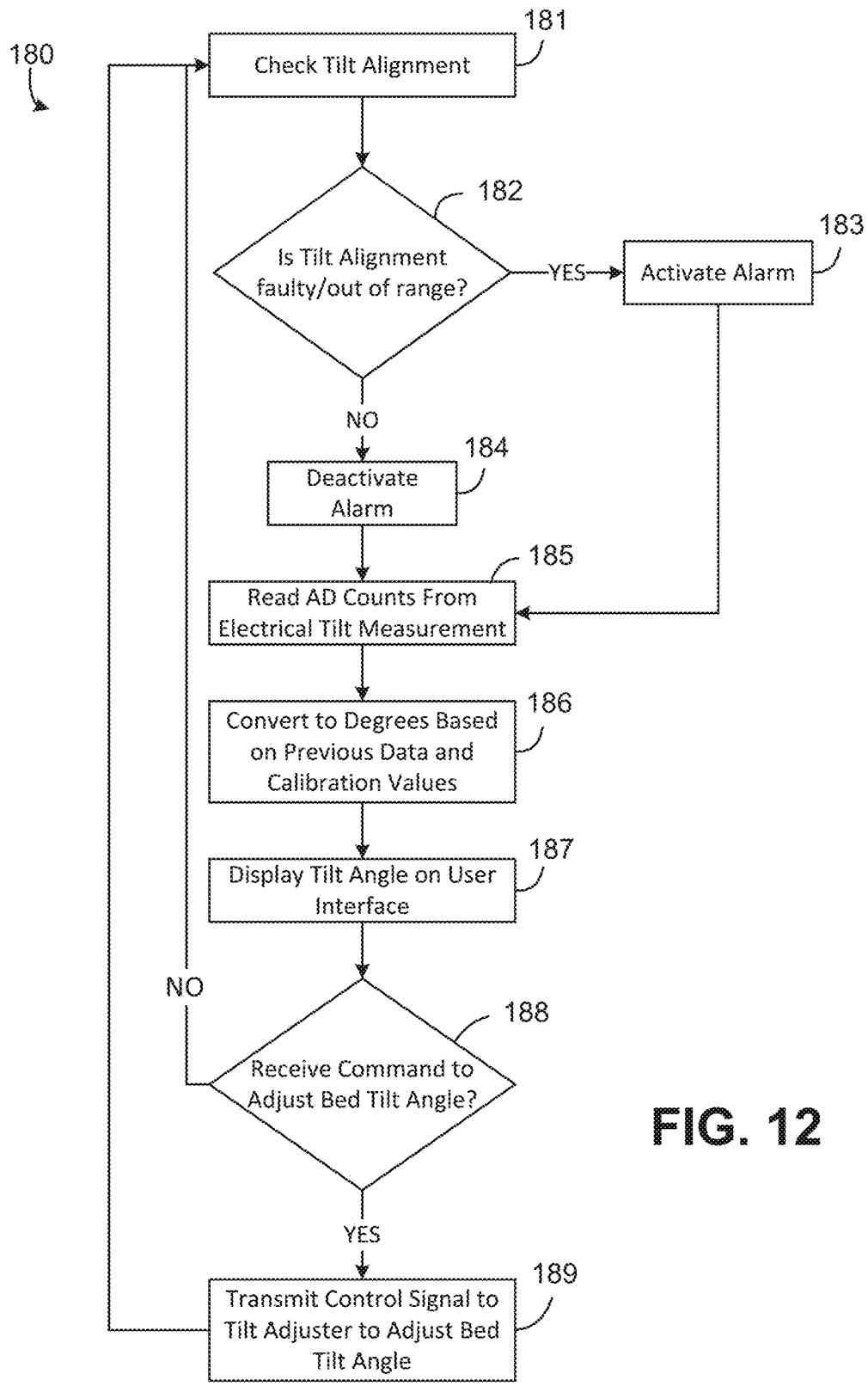
FIG. 12 is a flow chart illustrating a method of measuring, displaying, and adjusting bed tilt of a neonatal warmer in accordance with a second embodiment of the present invention.

FIG. 12 illustrates a process 180 for displaying bed tilt information and controlling bed tilt of the neonatal warmer 4 from the computing system 14. At the outset, the computing system 14 checks the tilt alignment of the neonatal warmer 4 and the bed tilt adjuster 6 (step 181). Using this information, the computing system 14 determines whether the tilt alignment of the neonatal warmer 4 and bed tilt adjuster 6 is faulty or beyond a predetermined range that is deemed acceptable (step 182). If the answer is yes, an alarm system is activated (step 183) before moving measuring the tilt of the neonatal warmer 4 (step 185). The alarm could be visual, auditory, or a combination of both. Alternatively, the alarm may be routed to a central monitor station so as avoid creating unnecessary noises or visual stimuli that may disturb the infant. If not, the computing system 14 simply moves on to step 185 while deactivating the alarm system if it is currently active (step 184). In step 185, the computing system 14 reads the raw tilt information (e.g., A/D counts) from the tilt sensor 8 to get a raw tilt measurement. This raw tilt measurement is then converted to degrees based on how the bed tilt adjuster 6 is calibrated and previously recorded data regarding bed tilt (step 186). The computing system 14 then displays the bed tilt angle on the user interface 16 (step 187). In an alternative embodiment, the computing system may present an option whereby the bed tilt angle is automatically adjusted back to level.

At this point, the computing system 14 checks whether it has received any commands from the user via the user interface 16 to adjust the bed tilt angle (step 188). If not, the computing system 14 returns to step 181. If so, the computing system 14 transmits, through the controller/processor 17, a control signal including those commands to the bed tilt adjuster 6 (step 189) before returning to step 181.

Figure 13:
FIG. 13 is an alternative embodiment of the display shown in FIG. 4, where the APGAR timer reads a time of 2:02, the stopwatch interface is missing and the environment monitor includes a bed tilt reading.
Figure 14:
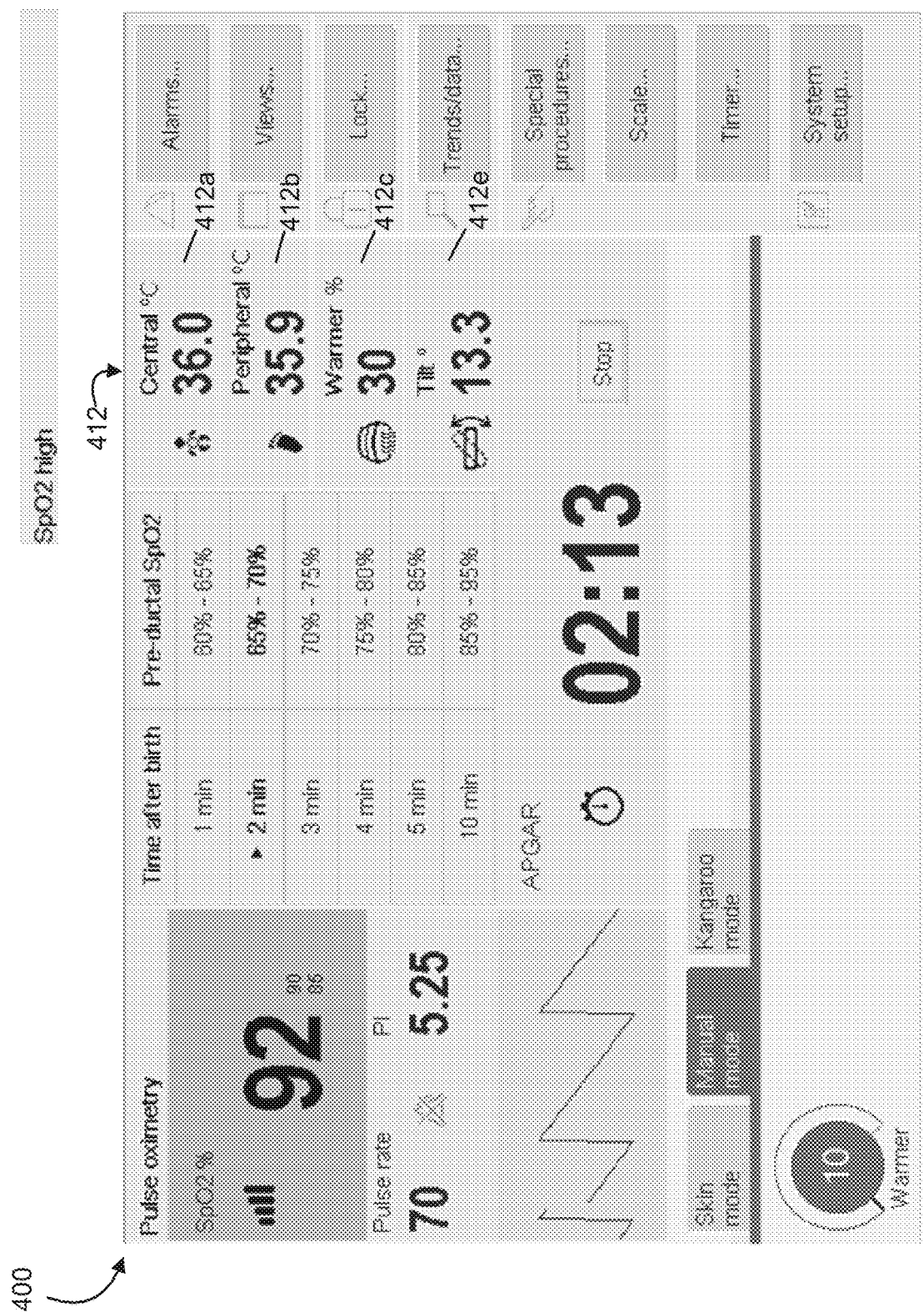
FIG. 14 is an alternate embodiment of the display shown in FIG. 4, where the APGAR timer is at a time of 2:13, the stopwatch interface is missing, the environment monitor includes a bed tilt reading, and an alarm being activated.

FIGS. 13 and 14 show alternative embodiments of the display 200 shown in FIG. 4. In the embodiment of a display 300 shown in FIG. 13, the sensor monitor 312 does not include a number of patient centric monitors, such as central and peripheral temperature, and instead includes only a warmer power monitor 312c and a bed tilt monitor 312e. The bed tilt monitor 312e shows the angle at which the bed of the neonatal warmer 4 is positioned relative to a horizontal plane. In the embodiment of a display 400 shown in FIG. 14, the sensor monitor 412 shows the same monitors as those shown in FIG. 4 (see, central temperature monitor 412a, peripheral temperature monitor 412b, and warmer power monitor 412c), except the mattress temperature monitor 212d is swapped for a bed tilt monitor 412e.

Figure 15:
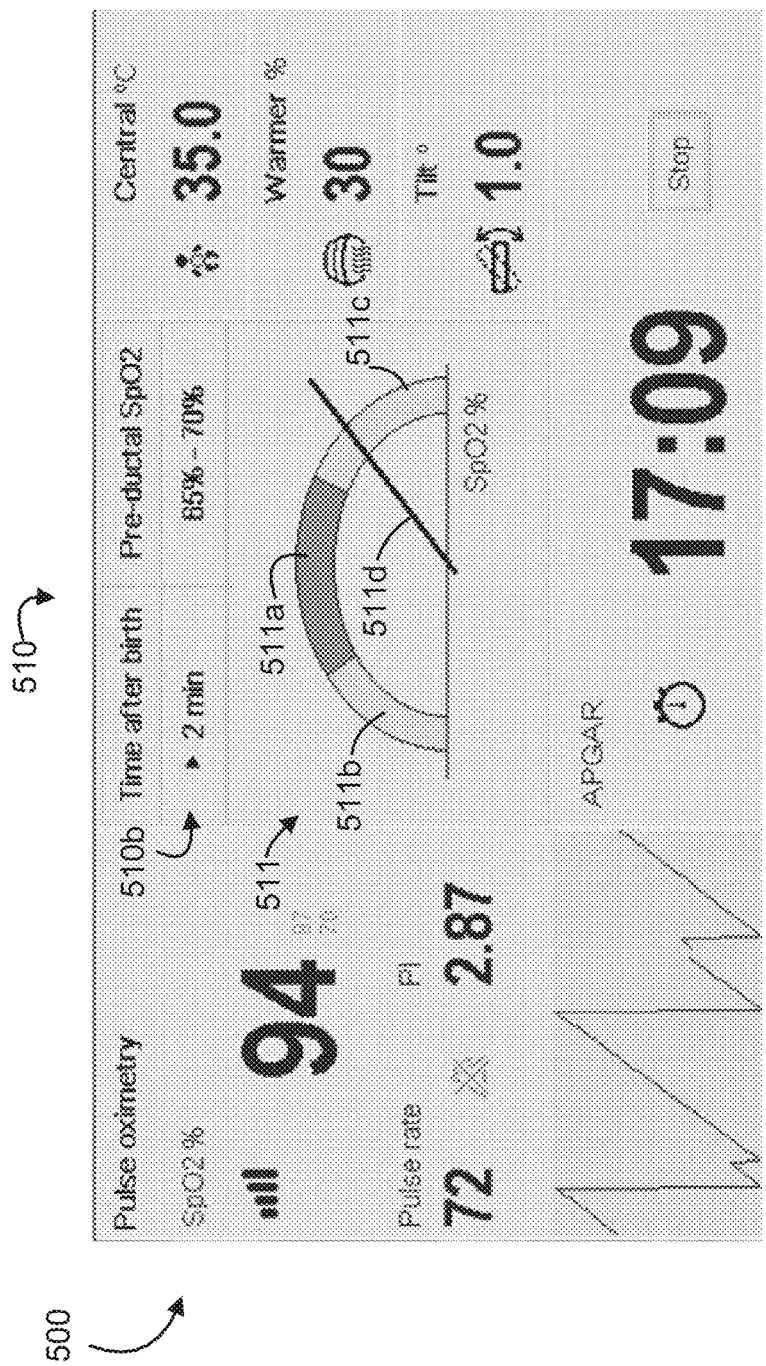
FIG. 15 is an alternative embodiment of the display shown in FIG. 4, where an entry in a target table has been selected to show where a measured blood oxygen value fell on a range of potential blood oxygen values.

FIG. 15 shows a third embodiment of a display 500. In this embodiment, the target table 510 is modified to have the table entries be selectable to show a greater understanding of where the measured SpO2 values fell within the target values at specific time windows. For instance, the target table 510 shows what happens when the second entry 510b associated with the second time window $T_2$ is selected. In such circumstances, the remaining entries of the target table 510 collapse, showing only the time window $T_2$ and target value $V_2$ information in the second entry 510b. Below the second entry 510b appears a target value gauge 511 showing a range of possible measured SpO2 values, with the range of values associated with the target value $V_2$ represented by a target band 511a shown in one color (e.g., green) and the range of values outside of the target value $V_2$ represented by a lower band 511b and an upper band 511c shown in a second color (e.g., yellow). The target value gauge 511 also includes a gauge wand 511d showing where the measured SpO2 value was in reference to the selected target value $V_2$ at a particular time during the selected time window $T_2$. The display 500 enables the user to get a graphical representation of where a neonatal patient's measured SpO2 values were in reference to the target value $V_x$ at any particular time, which can facilitate readily understanding the patient's health status at that time relative to what is expected of a healthy infant.

Figure 16:
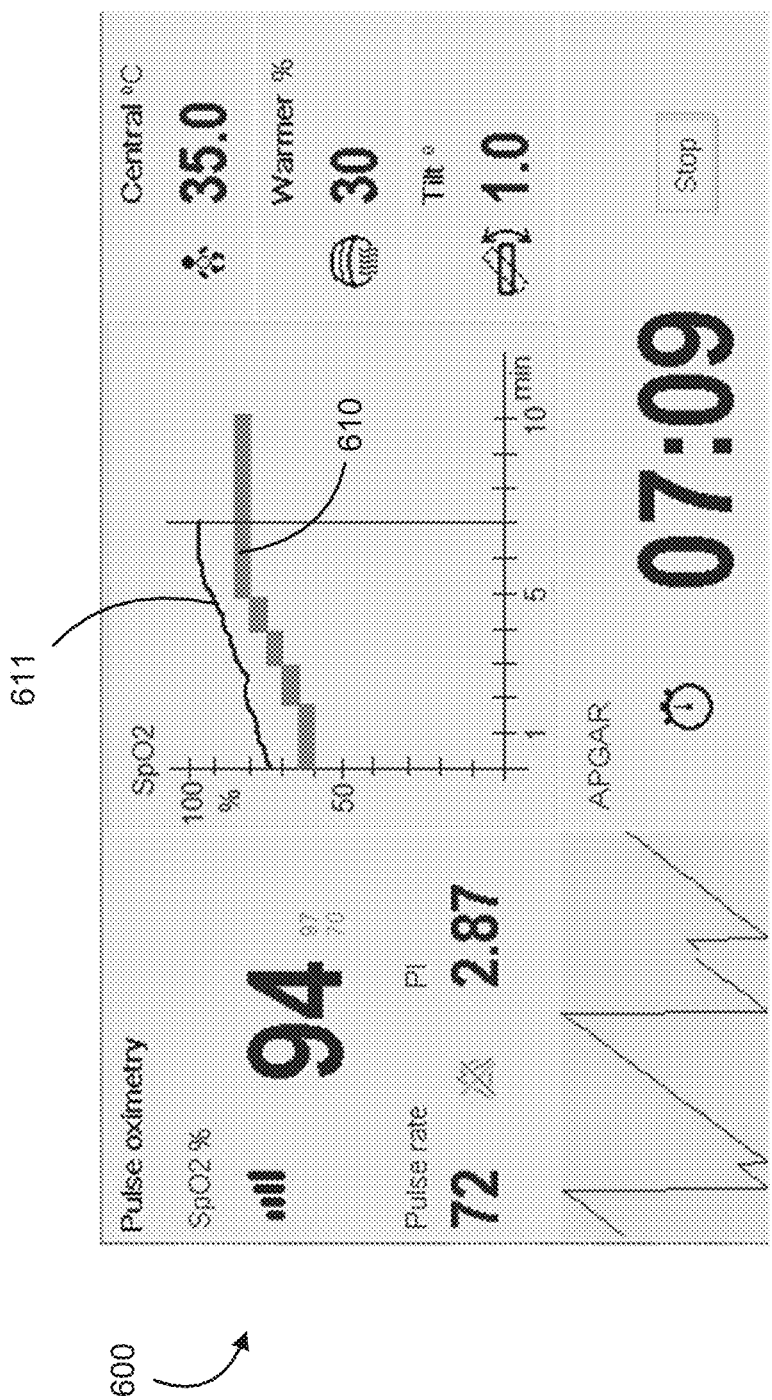
FIG. 16 is an alternative embodiment of the display shown in FIG. 4, where the target table and measured blood oxygen values are shown in a line graph.

FIG. 16 shows a fourth embodiment of a display 600. In this embodiment, a target graph 610 is provided instead of a target table and the measured SpO2 values 611 are presented in graphical format. Optionally, the color of the target graph 610 could be controlled to indicate whether the current measured SpO2 value 611 is within the target range. For example, target graph 610 could be green when the current measured SpO2 value 611 is within the target range and yellow if the current measured SpO2 value 611 is outside of the target range. The display 600 enables the user to visualize over time both the neonatal patient's measured SpO2 values and their relationship to the target values (represented by the target graph 610).

Figure 17:
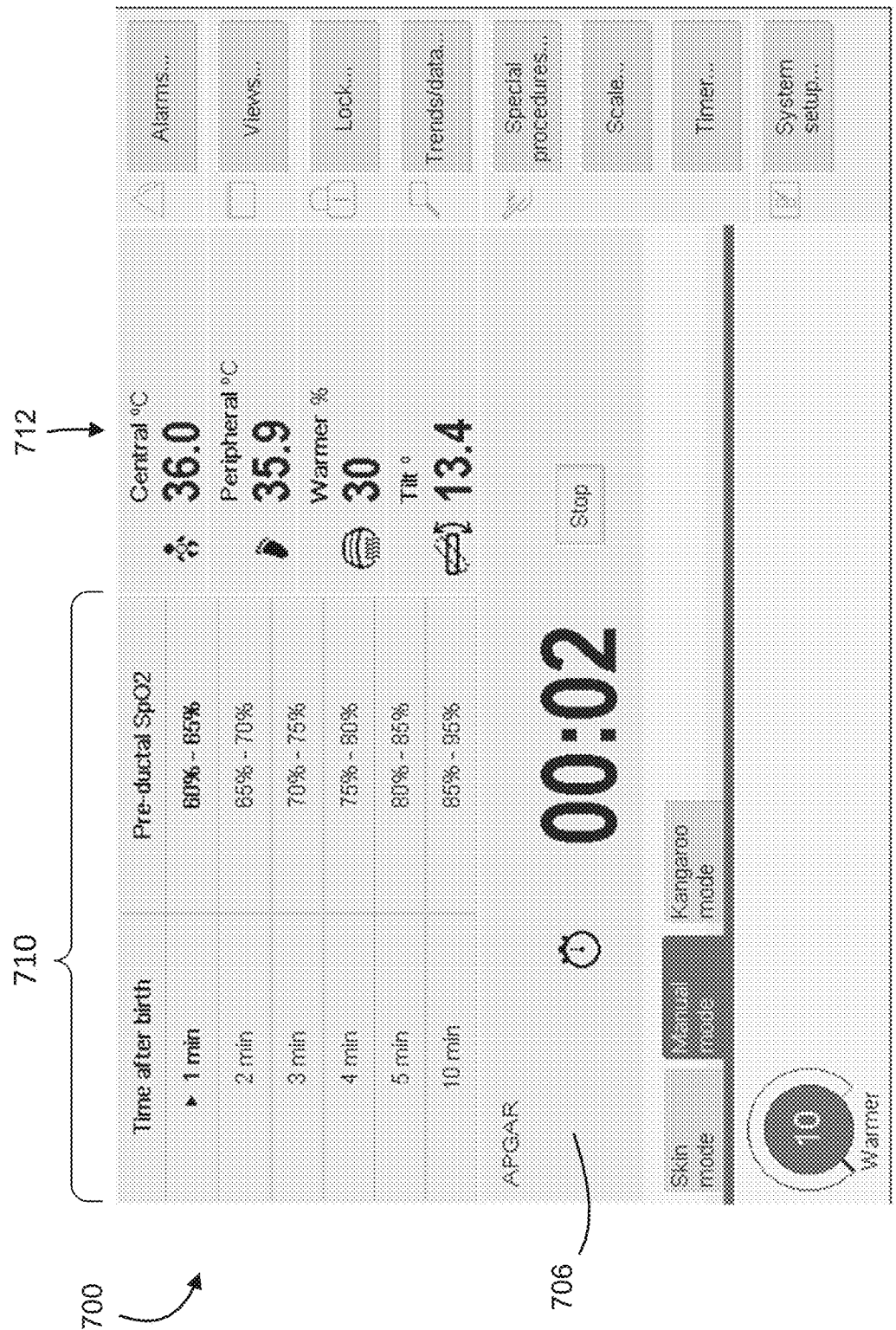
FIG. 17 is an alternative embodiment of the display shown in FIG. 4, where the measured blood oxygen value is omitted.

FIG. 17 shows a fifth embodiment of a display 700. This embodiment is very similar to the display 400 shown in FIG. 14, but omits the measured SpO2 or electrocardiogram monitors. This results in a simplified appearance that enables the other elements (the target graph 710, the APGAR timer 706, and the sensor monitor 712) to be larger. This display 700 may be desirable prior to the APGAR timer 706 being started and soon thereafter, when there is little measured SpO2 data.

It is important to note that the systems 10, 11 are not currently designed to provide automatic controls for providing supplemental oxygen to a neonatal patient, although these features could be implemented in the future. While it is possible to connect the systems 10, 11 to such a blood oxygen supplemental device, the current purpose of the systems 10, 11 is to provide information to a user in a way that focuses the user's attention on the essential health information of a neonatal patient. This allows a user to quickly and readily understand the essential information about an infant's health so that the user can make informed decisions quickly during the first critical minutes of an infant's life.

All examples and conditional language recited herein are intended for pedagogical purposes to aid the reader in understanding the principles of the present invention and the concepts contributed by the inventor in furthering the art. As such, they are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

It is to be understood that the embodiments described herein are merely exemplary and that a person skilled in the art may make many variations and modifications without departing from the spirit and scope of the invention. All such variations and modifications are intended to be included within the scope of the invention, as defined by the following claims.

The invention claimed is:

1. A method of displaying neonatal health information comprising:
    (a) receiving data characterizing a start of an APGAR timer;
    (b) storing information associated with a plurality of time windows and at least one target value associated with each of the plurality of time windows, each at least one target value representing a minimum target blood oxygen concentration during that time window;
    (c) receiving and displaying a time value representing a current time of the APGAR timer;
    (d) receiving a measured blood oxygen level value representative of the blood oxygen value at the current time of a neonatal patient using at least one physiological sensor;
    (e) displaying on an electronic display the measured blood oxygen level value at the current time in a numbered format;
    (f) displaying on the electronic display at least one of the plurality of time windows, wherein each of the plurality of time windows comprises a row of a table, wherein each row comprises a respective time window of the plurality of time windows and the minimum target blood oxygen concentration during that time window, wherein the measured blood oxygen level is displayed separately from the plurality of time windows of the table;

(g) highlighting, on the electronic display, a portion of the table that shows a selected time window of the plurality of time windows and the at least one target value associated with the selected time window when the current time of the APGAR timer is within the selected time window, wherein the highlighting makes stand out the minimum target blood oxygen concentration for the current time from the minimum target blood oxygen concentrations for the other time windows, comparing the measured blood oxygen level value at the current time with the minimum target blood oxygen concentration associated with the selected time window, and activating an alarm when the measured blood oxygen level value within the selected time window falls below the minimum target blood oxygen concentration associated with the selected time window, and further comprises changing the highlighting from the selected time window to another time window of the plurality of time windows when the current time of the APGAR timer changes to the another time window; and (h) repeating steps (c) through (g) at least until each of the plurality of time windows has been highlighted pursuant to step (g).

2. The method of claim 1, further comprising: (i) receiving data representative of an upper blood oxygen saturation limit and a lower blood oxygen saturation limit; and (j) activating the alarm when the measured blood oxygen level value exceeds either the upper blood oxygen saturation limit or the lower blood oxygen saturation limit;

wherein the alarm is configured to activate if the measured blood oxygen level value exceeds the at least one target value for the selected time window.

3. The method of claim 2, further comprising displaying the upper blood oxygen saturation limit and the lower blood oxygen saturation limit on the electronic display.

4. The method of claim 1, further comprising prompting a user to enter the plurality of time windows and the associated plurality of target values.

5. The method of claim 1, wherein step (f) comprises displaying on the electronic display the plurality of time windows arranged in an array of adjacent windows.

6. The method of claim 1, further comprising:
(k) receiving data representative of a start of a stopwatch timer;
(l) receiving a command to record a stopwatch time value; and
(m) storing the stopwatch time value and the measured blood oxygen level value.

7. A system for analyzing and displaying infant health information, the system comprising: at least one physiological sensor configured to obtain health information from a neonatal patient;
an APGAR timer;
a memory configured to store health information including a plurality of minimum target blood oxygen concentrations and health information from the at least one physiological sensor, each of the plurality of minimum target blood oxygen concentrations being associated with one of a plurality of time windows, the health information from the at least one physiological sensor including measured blood oxygen level values at the current time for the neonatal patient, wherein each of the plurality of time windows comprises a row of a table, wherein each row comprises a respective time window of the plurality of time windows and the minimum target blood oxygen concentration during that time window;

an electronic display having a user interface for receiving commands from a user and displaying the at least one of the plurality of time windows of the table and displaying the measured blood oxygen level value at the current time in a numbered format, wherein each of the measured blood oxygen levels is displayed separately from the plurality of time windows of the table; and at least one processor being in electrical communication with the at least one physiological sensor, the APGAR timer, the memory, and the electronic display, the at least one processor being configured (a) to highlight a portion of the table that shows a selected time window of the plurality of time windows and the minimum target blood oxygen concentration associated with the selected time window to be displayed on the electronic display when the current time of the APGAR timer is within the selected time window, wherein the highlighting makes stand out the minimum target blood oxygen concentration for the current time from the minimum target blood oxygen concentrations for the other time windows, comparing the measured blood oxygen level value at the current time with the minimum target blood oxygen concentration associated with the selected time window and further comprises changing the highlighting from the selected time window to another time window of the of the plurality of time windows when the current time of the APGAR timer changes to the another time window and (b) to activate an alarm when the measured blood oxygen value within the selected time window falls below the minimum target blood oxygen concentration associated with the selected time window.

8. The system of claim 7, wherein the memory is further configured to store a plurality of maximum target blood oxygen concentrations, each of the plurality of maximum target blood oxygen concentrations being associated with one of the plurality of time windows and the at least one processor is configured to activate the alarm if the measured blood oxygen value within the selected time window falls either below the minimum target blood oxygen concentration associated with the selected time window or above the maximum target blood oxygen concentration associated with the selected time window.

9. The system of claim 7, wherein the alarm comprises a visual indication on the electronic display.

10. The system of claim 7, wherein the at least one processor is configured to cause the maximum target blood oxygen concentration associated with the selected time window to be displayed on the electronic display when the current time of the APGAR timer is within the selected time window.

11. The system of claim 7, wherein the at least one processor is configured to cause all of the plurality of minimum target blood oxygen concentrations and all of the plurality of time windows to be displayed on the electronic display and to highlight the selected time window and the minimum target blood oxygen concentration associated with the selected time window on the electronic display when the current time of the APGAR timer is within the selected time window.

12. The system of claim 11, wherein the at least one processor is configured to cause all of the plurality of maximum target blood oxygen concentrations to be displayed on the electronic display and to highlight the maximum target blood oxygen concentration associated with the selected time window on the electronic display when the current time of the APGAR timer is within the selected time window.

13. The system of claim 11, wherein the at least one processor is configured to cause all of the plurality of minimum target blood oxygen concentrations and all of the plurality of time windows to be displayed on the electronic display in a graphical format.

14. The system of claim 7, further comprising a stopwatch timer, wherein the at least one processor is configured, in response to a user comment, to record in the memory a stopwatch time value and a measured blood oxygen value corresponding to the stopwatch time value.

* * * * *